(12) United States Patent
Haar et al.

(10) Patent No.: US 8,394,035 B2
(45) Date of Patent: Mar. 12, 2013

(54) MULTI-LANCET DEVICE

(75) Inventors: Hans-Peter Haar, Wiesloch (DE); Herbert Harttig, Neustadt (DE); Joachim Hoenes, Zwingenberg (DE); Hans-Juergen Kuhr, Mannheim, DE (US); Ortrud Quarder, Heidelberg (DE); Dirk Voelkel, Weinheim (DE); Volker Zimmer, Laumersheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 695 days.

(21) Appl. No.: 12/356,908

(22) Filed: Jan. 21, 2009

(65) Prior Publication Data

US 2009/0177118 A1 Jul. 9, 2009

Related U.S. Application Data

(63) Continuation of application No. PCT/EP2007/006482, filed on Jul. 20, 2007.

(30) Foreign Application Priority Data

Jul. 21, 2006 (EP) ..................................... 06015187

(51) Int. Cl.
*A61B 5/00* (2006.01)
(52) U.S. Cl. ....................................... 600/583; 606/183
(58) Field of Classification Search .................. 206/364, 206/365; 600/557, 583; 606/181–183
See application file for complete search history.

(56) References Cited

U.S. PATENT DOCUMENTS

| | | | |
|---|---|---|---|
| 2,896,628 A | 7/1959 | Speelman | |
| 3,517,670 A | 6/1970 | Speelman | |
| 3,789,830 A | 2/1974 | Malmstrom | |
| 4,412,548 A * | 11/1983 | Hoch | ............................ 600/577 |
| 4,545,376 A | 10/1985 | Beiter | |
| 5,730,753 A | 3/1998 | Morita | |
| 6,132,449 A | 10/2000 | Lum et al. | |
| 6,156,051 A | 12/2000 | Schraga | |
| 6,176,865 B1 | 1/2001 | Mauze et al. | |
| 6,306,152 B1 | 10/2001 | Verdonk et al. | |

(Continued)

FOREIGN PATENT DOCUMENTS

| | | |
|---|---|---|
| EP | 1 491 142 A1 | 12/2004 |
| EP | 1 508 304 A1 | 2/2005 |

(Continued)

*Primary Examiner* — Max Hindenburg
(74) *Attorney, Agent, or Firm* — Bose McKinney & Evans LLP

(57) ABSTRACT

The invention concerns a device for collecting body fluids which has at least one lancet comprising a lancet body with at least two tips of different lengths. The device is characterized in that it has a selection means with the aid of which only one tip is selected before the lancing. This selection means can have different functions and shapes. The selection means is used to select a tip from a plurality of lancet tips which have different lengths and make only this tip available for use in the lancing process. Since the various tips are attached to a lancet body, it is, for example, possible to use a bending element which bends one of the various tips out of the plane of the lancet body in order to provide only one lancet tip for use. This is especially preferable for lancet tips that are arranged linearly relative to one another.

31 Claims, 5 Drawing Sheets

U.S. PATENT DOCUMENTS

| | | |
|---|---|---|
| 6,589,202 B1 | 7/2003 | Powell |
| 6,726,649 B2 * | 4/2004 | Swenson et al. ............... 604/46 |
| 6,924,087 B2 | 8/2005 | Yeshurun et al. |
| 6,929,650 B2 | 8/2005 | Fukuzawa et al. |
| 7,670,352 B1 * | 3/2010 | Starnes ....................... 606/181 |
| 7,678,126 B2 * | 3/2010 | Schraga ....................... 606/181 |
| 7,901,362 B2 * | 3/2011 | Freeman et al. ............. 600/583 |
| 7,909,776 B2 * | 3/2011 | Roe et al. ..................... 600/583 |
| 2005/0171567 A1 | 8/2005 | DeHart |
| 2009/0187118 A1 * | 7/2009 | Kim et al. .................... 600/583 |

FOREIGN PATENT DOCUMENTS

| | | |
|---|---|---|
| GB | 1 211 432 | 11/1970 |

* cited by examiner

MULTI-LANCET DEVICE

RELATED APPLICATIONS

This application is a continuation application of International Application PCT/EP2007/006482, filed Jul. 20, 2007, which claims priority to EP 06 015 187.5, filed Jul. 21, 2006, which are incorporated by reference in their entirety.

BACKGROUND

The invention relates to the field of lancing aids for the diagnostic determination of blood parameters. Body fluids are collected and analysed in many fields of medical diagnostics. It is therefore desirable to also enable routine tests to be carried out rapidly and reproducibly outside the laboratory. The testing can be carried out with various body fluids such as, e.g., blood and/or interstitial fluid. These fluids can be analysed for various characteristics. The results of this analysis are important in order to be able to make reliable diagnoses and to carry out therapeutic measures and therapeutic monitoring.

The analysis of body fluids begins with the collection of fluid. One method of collecting body fluid is to generate a minimal wound in the skin of a patient with the aid of a needle, lancet or knife. The body fluid obtained in this process can either be collected in small vessels or directly brought into contact with a test element such as, e.g., a test strip for analysis. Most of these lancing aids require the lancet to be manually inserted into the lancing aid. This handling is very laborious when the lancing aid is used frequently. The storage of lancets in magazines can eliminate this problem but in this case many safety aspects have to be observed. Care should, for example, be taken to safeguard the safety of the patient when the lancing aid is used. Moreover, the system should not become too complex because it would otherwise not be easy to operate by the patient. Another important feature apart from storage in magazines is the possibility of adjusting the lancing depth before the lancing process. This can be ensured by the device as, for example, described in publication WO 2006038044. The adjustment of the lancing depth by the device requires a complicated mechanism because the lancet drive and the lancing depth adjustment control mechanism must be adapted to one another. Alternatively, the lancing depth could also be controlled by the lancets.

Although lancing aids are described in the prior art which have more than one lancet, in these cases it is not possible for the user to influence the lancing depth before lancing. A lancet system is, for example, described in U.S. Pat. No. 4,794,926 in which a plurality of lancets that can be used individually for the lancing process is stored on a base body. However, this system does not offer any possibility for the patient to select the lancing depth before the lancing process.

SUMMARY OF THE INVENTION

The present invention provides a lancing aid which is easy to handle and cost-effective to produce and at the same time enables a simple adjustment of lancing depth.

The invention concerns a device for collecting body fluids which has at least one lancet comprising a lancet body with at least two tips of different lengths. The device is characterized in that it has a selection means with the aid of which only one tip is selected prior to the lancing. This selection means can have different functions and shapes. The selection means is used to select one tip from a plurality of lancet tips of different lengths and to make only this tip available for use in the lancing process. Since the lancet tips have different lengths, the lancing depth can be adjusted by selecting the lancet tip to be used for the lancing process. During the lancing process itself the selected lancet tip and the other lancet tips are arranged such that only the selected lancet tip penetrates into the body to be punctured.

This device for collecting body fluid has the advantage that no further adjustment of the lancing depth has to be carried out on the device itself as is the case in the device described in, e.g., publication WO 20060380449. As a result, the drive does not have to be specially adapted to the lancing depth control of the device. No adjustable parts need be attached to and adjusted on the device itself. As a consequence, it is possible to use cost-effective drives and housings.

In the device described herein, the lancing depth is thus selected by means of the selection of the lancet tip. This means that a plurality of lancet tips of different lengths is provided. These lancet tips of different lengths are arranged on a lancet body. The type of arrangement can encompass all possible shapes and geometries. Thus, the lancet tips can be arranged linearly where the tips can point in the same or in opposite directions. However, the lancet tips can also point non-linearly in different directions by being, for example, arranged at different angles on the lancet body. One embodiment with different lancet tips which are arranged in different directions on the lancet body is a star-shaped arrangement of the tips. In one embodiment, the lancet tips are attached to the lancet body in one plane.

After a certain lancet tip has been selected, the individual tip can be used by moving the lancet body in such a manner that only one lancet tip points in the direction of the body to be punctured when the lancet body is moved. The other lancet tips point in other directions and are consequently not also inserted into the body during the lancing process. This arrangement of selected and unselected tips can be achieved in various ways by means of different geometries of the lancet body. Different means for selection are necessary for this.

Different means for selecting the tip to be used can be provided for different arrangements of lancet tips. These selection means can, for example, comprise a mark on the lancet itself or on the lancet body. Such a mark can, for example, be detected optically, mechanically or electrochemically in the device. A sensor can be used for this which enables an optical, mechanical or electrochemical registration of the arrangement of the lancet body in the device. This mark can, for example, be a notch or a coloring of a part of the lancet or of a possible carrier if the lancet is mounted on a carrier.

Furthermore, the selection means can be a device which enables the lancet body to be positioned in such a manner that the lancet tip selected for use is made available so that it can interact with the drive unit in order to be moved for the lancing. This can, for example, be the same device which is also used to advance the lancet body by one step. At each advance the lancet body is shifted further by one lancet tip. This can be indicated to the user by a counter so that it is always apparent to the user which lancet length is currently being made available for the lancing. In this connection, a reversal of the device's stepping action should be prevented so that a repeated use of a lancet tip is impossible. However, any other type of selection is also possible which ensures a positioning of the lancet body in order to select an individual lancet tip for use and to position it relative to the drive unit for the lancing in such a manner that not more than one lancet tip is used. Also, in the case of a star-shaped arrangement of lancet tips on the lancet body and an arrangement of different tips at different angles on the lancet body, it is possible to make an optical or mechanical mark as described above. Other possibilities of marking the lancet body are a different magnetization or different impedance of different regions of the lancet body or of the lancet tips. In the case of an optical identification of the lancet body or of the individual lancet tips, the device requires an optical identification means such as, for example, an optical sensor. In contrast, when the positioning of the lancet body is detected mechanically, a catch mechanism is, for example, required which enables the lancet body and thus the lancet tips to be exactly positioned by means of notches in the lancet body. Irrespective of how the lancet tip selected by the user is selected, the selection should result in an exact positioning of the lancet body. The selection and subsequent exact positioning of the lancet body ensure that the drive unit moves the lancet body in such a manner that only the selected lancet tip penetrates into the body.

If positioning is referred to in this connection, then this means the positioning of the selected lancet tip or the lancet body relative to the drive unit and to the lancing site. Hence, it should be ensured that the selected lancet tip can be moved by the drive unit so that the body part provided for the lancing can be punctured.

As an alternative to marking a part of the lancet or of the carrier of the lancet, the carrier or the lancet can be positioned in the device so exactly that the selected lancet tip can be provided for use solely by rotating and/or displacing the lancet body or carrier.

Since the various tips are attached to a lancet body, it is, for example, possible to use a bending element which bends one of the different tips out of the lancet body plane in order to make only one lancet tip available for use. This is particularly preferred in the case of lancet tips that are arranged linearly relative to one another. In this connection the bending element is the selection means. The bending enables only the bent lancet to be moved towards the body part to be punctured when the lancet body is moved for the lancing. Consequently, the bending prevents more than one lancet tip from penetrating into the body.

An alternative to bending the selected lancet tip is to space the lancet tips sufficiently apart so that one tip can be positioned and used without other tips penetrating into the body, although all tips are also arranged in the same direction on a lancet body. Even if all lancet tips are moved simultaneously in the lancing process, the spacing can ensure that only one lancet tip penetrates into the body. Consequently, in this case the selection means can be realized due to an adequate spacing of the lancet tips. Thus, the lancet body advantageously has a plurality of coupling elements which enable the lancet to be coupled to the drive unit at various positions on the lancet body. Accordingly, the lancet tip which is to be used for a lancing process is selected depending on the selected coupling element. Consequently the coupling elements are a component of the selection means in this described embodiment.

If it is intended to bend the lancet tip away from the lancet body, then the lancet should have particular material properties. Thus, the lancet can, for example, be a flat lancet and/or have a bending region. In one embodiment, the lancet is a flat lancet and has a bending region. In another embodiment, the lancet body also has a flat shape. The bending region of the lancet which can be located outside the tip region has at least one structure with an altered stiffness. This at least one structure with an altered stiffness is referred to in the following description as an "impression." The impression can, for example, be worked into or onto the lancet by, for example, etching, punching or hammering or other metal working measures. The stiffness can also preferably be adjusted by varying the geometry of the lancet or by varying the amount of material for producing the lancet. A preferred embodiment comprises more than one impression in the bending region of the lancet. A particularly preferred embodiment of this impression is a triple impression in the bending region of the lancet which extends over at least a part of the longitudinal extension of the lancet. In this case an impression extends from the distal end of the lancet in an axial direction towards the proximal end of the lancet. The length of the impression is variable. This impression can be introduced into the lancet from two sides. These differences in the direction of the impression have the effect that the lancet tip is bent away in the opposite direction to the lancet body. As a result, the bent areas are lifted out of the lancet body plane at an angle of preferably up to 100°. Thus, the lancet tip is moved out of the plane of the lancet body.

Force can be transferred onto the lancet by a bending element, e.g., a pusher which is pressed onto the lancet. In an embodiment comprising more than one impression, force can be transferred onto the lancet by, for example, guiding the lancet body with the lancet tip over the pusher or pressing the pusher against the lancet tip. In this process, an adequately large force (threshold force) acts on the lancet to move the lancet tip out of the lancet body plane. If the lancet body is a carrier tape or if the lancet body is attached to a carrier tape, it may be necessary to bend the lancet tip back again into the carrier tape plane after the lancing so that it can be stored again in a magazine. A resetting element which, after the lancing, transfers the lancet tip back into its original position before the bending as shown in FIGS. 8 a-d can be used for this. Furthermore, it can be re-stored in a magazine as a result of the material properties of the lancet. Thus, the lancet can, for example, be manufactured from a shape-memory material such as, for example, Nitinol which can be bent in a cool state (such as, for example, at room temperature) and retains its bent form until it is heated. This bending-back temperature is between 34-60° C., depending on the alloy.

One embodiment for the arrangement of the lancet tips of different lengths is a lancet wheel. In this case lancets are arranged circularly in a plane and their lancet tips have different lengths or are bent at different positions in order to vary the length of the lancet tip. In this case the lancet tip can also be in the form of a blade.

The material of the lancet can be metal, particularly steel. The lancet can, however, also consist of other materials and combinations of materials. Furthermore, the material should be such that it can be worked into a sharp tip at the distal end of the lancet tip, since too much pain would otherwise be generated during the lancing. The production of lancets in general is adequately known in the prior art, for example, in DE 19604156 or EP 0565970. If the lancet is bent before the lancing process, the material of the lancet should be such that the lancet can be bent when a force acts on it but has sufficient stiffness to penetrate into the skin when used without changing its shape. In one embodiment, the lancet body together with the lancet tips is worked in one piece. This can, for example, be generated by etching or stamping the lancet out of steel.

Various methods can be used to actuate the lancet. The choice of method depends above all on the geometry of the device. Thus, the device may solely drive one lancet, or the device can be combined in a system together with further elements such as test elements, detectors, evaluation units and display units. In one embodiment, a plurality of lancet bodies with a plurality of test elements are arranged on or in a carrier tape. In this case the carrier tape can act as a lancet body. The proximal end of the lancet can, for example, be attached to the carrier tape in such a manner that a part of the lancet can be moved relative to or with the carrier tape, whereas the proximal end is connected at least one point to the carrier tape. Another means of attachment of the lancet is to attach the lancet body to the carrier tape where the tip region disengages from the carrier tape. A controlled movement of the lancet can be achieved by moving the carrier tape or by gripping the lancet with a gripping element, whereupon the lancet tip together with the carrier tape is moved out of the plane of the carrier tape. This movement can be executed by means of a drive element which transfers force onto the lancet perpendicularly to the carrier tape plane. The force is transferred by a drive element, which, for example, can be a pusher or a gripping element which grips and moves the lancet body of the lancet. In this connection, the lancing depth of the blood collection device can be chosen at will. In addition to the length of the lancet tip, it is possible to define the movement of the lancet by a variable stop element against which the lancet strikes during the lancing process in order to adjust the lancing depth. In this manner the length of the lancet tip which is inserted into the body and thus the lancing depth varies depending on the position of the stop element. The stop element can, for example, be integrated into the housing. Furthermore, the lancet itself can serve as a stop element where the lancing depth is defined by the length of the tip which protrudes from or is bent away from the lancet body. In this case, the lancet body is a barrier to further penetration of the lancet into the skin.

Ballistic mechanisms or mechanisms guided by guide blocks which are known from the prior art and described, for example, in DE 19604156, EP 0565970, U.S. Pat. No. 5,318,584 or U.S. Pat. No. 4,924,879 can be used to drive the lancet. One embodiment for the lancet drive is the free movement of the lancet after force has been transferred by the drive element such as, for example, the pusher. In this embodiment an impulse is transferred from the drive element onto the lancet and the lancet moves towards the housing opening without further guidance by the drive element. In this case the movement of the lancet can be guided by additional elements on the housing.

In order to use the system hygienically, the lancet can be protected by a sterile protection at least in the tip region of the lancet. This sterile protection can be a foil which additionally contains an antibacterial agent such as, for example, silver. The entire lancet body of the lancet is preferably covered with this foil as a sterile protection. When a carrier tape is used, the foil can also extend over a part of the carrier tape and be connected thereto. This sterile protection can also consist of a polymer layer which is applied after the lancet has been manufactured. This polymer layer is destroyed or pierced by the lancet tip to expose the lancet tip when the threshold force is applied to the lancet tip. Alternatively, the sterile protection can be removed before using the lancet. In this case the sterile protection is preferably entirely removed.

In one embodiment, the lancet has a channel at least in its tip region which serves to collect blood from the wound with the lancet. This embodiment is referred to in the following as a microsampler. The blood collected in the microsampler can subsequently be transferred onto a test element and detected by a detection system (e.g., optically or electrochemically) and evaluated by an evaluation system.

Also described herein is a lancet for insertion into a body part. The lancet body has at least two tips which have different lengths. The lancet is designed such that a tip can be selected so that a lancing process can take place with a defined lancing depth that depends on the length of the selected tip. Furthermore, the unselected tips can be positioned relative to the selected tip during a lancing process in such a manner that a lancing process is only carried out with the selected tip, whereas the unselected tip is not involved in the lancing process. In this manner, the lancing depth can be adjusted by selecting a particular tip of a lancet. For example, a lancet tip can be selected by bending a tip where the lancet has a bending region for this purpose as already described. It is, however, also possible to design a coupling element of a lancet such that a drive unit can dock at different positions on the lancet or the lancet is coupled at different positions on the drive unit so that, as a result, a tip is selected for carrying out the lancing process. In general, a coupling element is understood as that part of the lancet which allows docking between the lancet and the drive unit of a device. For example, a coupling element can comprise a recess in the lancet body into which a drive unit can engage. However, other designs are also possible such as, e.g., a structuring of the lancet body as is already well-known in the prior art and has been described for systems which allow a replaceable lancet to be coupled to a blood withdrawal system. Moreover, a plurality of coupling elements of a lancet is also conceivable so that a tip can be selected by selecting an appropriate coupling element. In the described embodiments, the coupling element of the lancet is then, for example, at the same time a component of a selection means as already described. In general, it is thus evident that, depending on the respective design of a system/device which is suitable for use of the lancet, a wide variety of embodiments of a coupling element are conceivable which advantageously also allow a lancet tip to be selected. Furthermore, the lancet can comprise additional means for selection as has already been described. Examples are marks on the respective lancet tips which, in an appropriate device, allow a specific selection of a lancet tip, e.g., by means of an optical detection of the mark and thus allow a selection of the lancing depth. Hence, in such systems, the selection means are advantageously a component of the device as well as of the lancet itself where an appropriate interaction between the device and lancet allows a lancet tip to be selected.

The invention also concerns a system for collecting body fluid. As already mentioned, the device can be combined in the system with further different elements for analysing a body fluid (e.g., test element, detector, evaluation unit, etc.). A system with a carrier tape is described as an example which, however, should not be interpreted as implying a limitation of the selection of elements in a system. This system may consist of a housing in which an essentially planar carrier tape is mounted, and of at least two lancets which lie on the carrier tape. The housing has at least one opening towards which the lancet is moved during the lancing process and if necessary, through which the lancet can pass. The essentially planar carrier tape is preferably wound onto two spools. However, other methods for storing used and unused lancets can also be utilized. If two spools are used to store the lancets, the unused lancets are on one spool and the used lancets are on the other spool.

The lancets consist of a material which is soft enough to be wound onto the carrier tape without being bent in this process. On the other hand, the material of the lancets is sufficiently stable that the lancets are not deformed during actuation and entry into the skin. Alternatively, the lancets are arranged transversely on the carrier tape to prevent a bending of the lancet. Another method of avoiding bending of the unused lancets is to select the diameter of the spool on which the lancets are stored such that the lancets are hardly bent when they are rolled up.

The lancet has at least two lancet tips which are located on the lancet body. After the user has selected the lancing depth, the lancet tip is made available for use by the selection means (in this case, a bending element). In this embodiment, the lancet is thus selected by bending. Because of the bending element which acts on the lancet in this manner, the alignment of the lancet tip relative to the remaining lancet body is changeable. When force acts on the lancet before the actuation, the bending element can control the position at which force acts on the lancet body. For this purpose, the bending element can be controlled by a control element. A pusher or folding-down lever can be used to transfer the force. Conventional lancets can be used in the system and the lancets are preferably in the form of flat lancets.

The lancet is moved by a drive element towards the housing opening in order to execute a lancing process there. In the case of a bent lancet tip this can take place after or during this bending process. In this process at least a part of the lancet bends towards the housing opening and pricks the skin of the patient. A drop of blood forms on the puncture site which is used for analysis. If a test element is located on the carrier tape, the carrier tape is transported, if required, far enough so that the test element is situated below the housing opening. The drop of blood can be applied to the test element without the patient having to initiate further steps. The blood reacts with one or more reagents which are located on the test element such as those that are known from the documents EP-A 0 885 591, EP-B 0 535 480 and EP-B 0 477 322. The test element is analysed by means of a detector.

The blood can be examined for various components as is known in the prior art. For example, the analysis can be directed towards blood components such as haematocrit, glucose, cholesterol, coagulation, iron and others. Different methods can be used for the analysis. Thus, for example, electrochemical detection reactions can be used and also optical (e.g., reflection, absorption, fluorescence, Raman spectroscopy) or magnetic detection reactions. Typically the liquid is brought into contact with a test system whereupon a reaction takes place between a test element and the liquid. Thus, detection by means of an optical test element is based on a colour reaction between the liquid and detection reagent. Examples of these reactions are described in the U.S. Pat. Nos. 3,802,842, 4,061,468 and 4,490,465.

When the device is used the system carries out various steps. A desired lancing depth is selected on the device. As a result of this selection the system selects a lancet which corresponds to the desired or preselected lancing depth with the aid of a selection means according to one of the selection mechanisms described above. If it is intended to bend the lancet before the lancing, it is moved into a position in which it can be brought into the bent state by the action of a threshold force on the lancet body. In this process the sterile protection is preferably ruptured. If the lancet is not bent before the lancing, then the sterile protection is removed before or during the lancing. If necessary, the lancet is transported to the opening of the housing where it is actuated with the aid of a drive element and part of it can emerge from the housing opening. During the actuation process, at least part of the lancet enters the skin of the patient and afterwards returns into the device.

If the lancet is on a carrier tape, this carrier tape can be advanced and wound onto the second spool. There the lancet again lies flat on the carrier tape. This re-storage process is described in U.S. Publication No. 2005/0245845.

In an integrated system in which test elements are also mounted on the carrier tape, preferably alternating with the lancets, the test element is transported after the lancing process to the housing opening in order to pick up the drop of blood for analysis. The test element can be transported to the detector and measured there.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawing, wherein.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
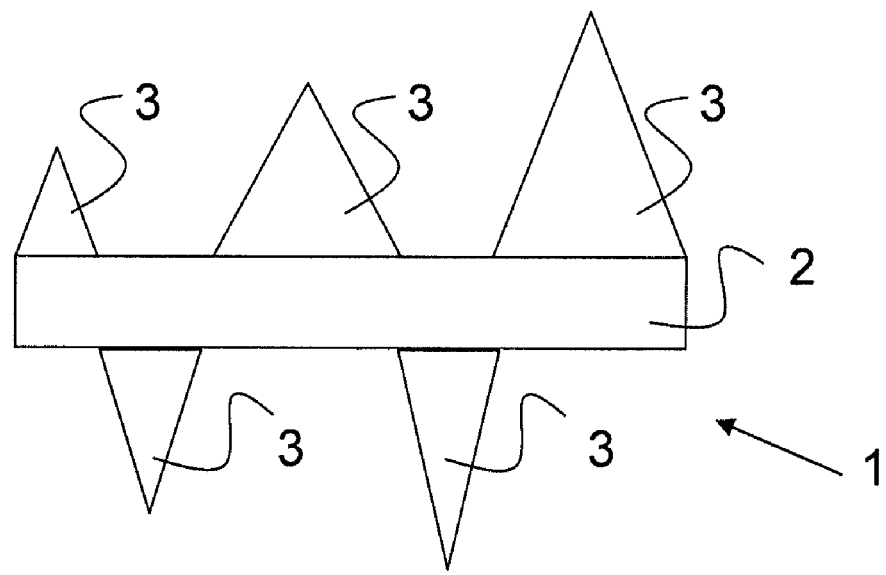
FIG. 1 is a schematic diagram of a lancet body with several lancet tips of different lengths which are attached to two sides of the lancet body.

FIG. 1 shows a lancet 1 which consists of a lancet body 2 and at least two lancet tips 3. In the arrangement shown in FIG. 1 some of the lancet tips 3 are located on one side of the lancet body 2 which is shown here as a rectangle and the remaining lancet tips 3 are located on the opposite side of the lancet body 2. Several hundred lancets can be arranged in such a tape-like structure of the lancet body 2. Up to 100 lancet tips 3 can be arranged on the lancet body which can then, for example, be wound onto a tape. In a further embodiment, up to 6 lancet tips 3 are arranged on the lancet body 2, in which case the lancet bodies can then be arranged in a stack-like manner in a magazine. If a carrier tape is used to store the lancet tips, it is also possible that the carrier tape serves as the lancet body on which the lancet tips are arranged. This carrier tape can, for example, consist of material or it can also be a metal tape. The means for selection, i.e., the selection of the lancet length and thus of the lancing depth can in this case be a device element which is used to advance the device in steps. An exactly adjusted mechanism conveys the tape in each stepping operation from one to the next lancet tip. For this purpose the lancet tips must be precisely arranged. At each advance the lancet body is shifted further by one lancet tip. This can be indicated to the user by a counter so that it is always apparent to the user which lancet length is currently being made available for the lancing. In this connection a reversal of the device's stepping action should be prevented so that a repeated use of a lancet tip is impossible.

Figure 2:
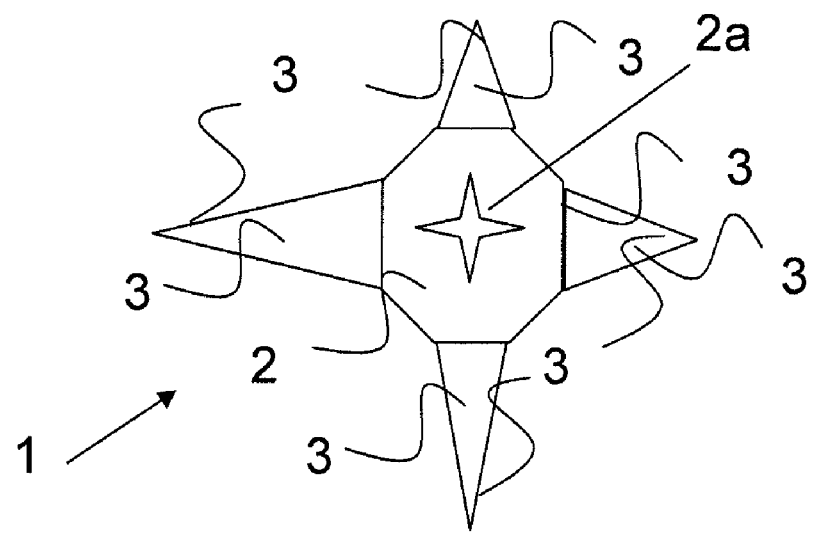
FIG. 2 is a schematic diagram of a star-shaped arrangement of lancet tips on a lancet body.

In FIG. 2, the lancet tips 3 are arranged at various angles to the lancet bodies 2. In this case the lancet tips 3 can point in all directions in space. The lancet tips 3 are preferably arranged in one plane so that the lancet 1 can be stored in a stack magazine without damaging the lancet tips. Depending on the geometry of the lancet body, up to 10 lancets can be arranged at various angles to the base body in this star-shaped arrangement, preferably there are 4 to 5 lancet tips 3. The lancet body preferably has a recess/hole 2a which is provided as a coupling element for coupling to an appropriately designed pusher (not shown) of a drive unit. In the example shown, the lancet is rotatably connected to the drive unit so that a desired tip for a lancing process can be selected by means of a rotation of the pusher and thus of the lancet. In this manner, a lancet tip can be selected due to an interaction of the drive unit with the coupling element of the lancet.

In one embodiment, the lancet tips 3 have a bending site at their proximal end 3a which adjoins the lancet body 2. This bending site enables the lancet tip 3 to be bent out of the plane of the base body and of the remaining lancet tips which enables the desired lancet tip 3 to be selected. In the lancing process the entire lancet 1 is used for the lancing process.

Figure 3:
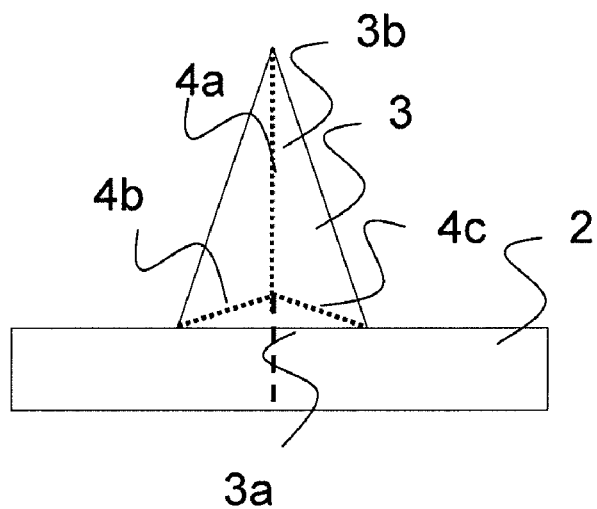
FIG. 3 is a schematic diagram of a bendable tip on the lancet body.

FIG. 3 shows a section of a lancet 1 where the lancet tip 3 located on the lancet body 2 has a region with several bending lines 4a, b, c. The bending line 4a extends from the distal end 3b of the lancet tip 3 towards the proximal end 3a of the lancet tip 3. In this case this bending line 4a can extend over the complete tip region for the lancet tip 3 or only over a subregion of the lancet tip 3.

Further bending lines 4b and 4c can extend laterally from the first bending line towards the proximal end 3a of the lancet tip 3.

Figure 4:
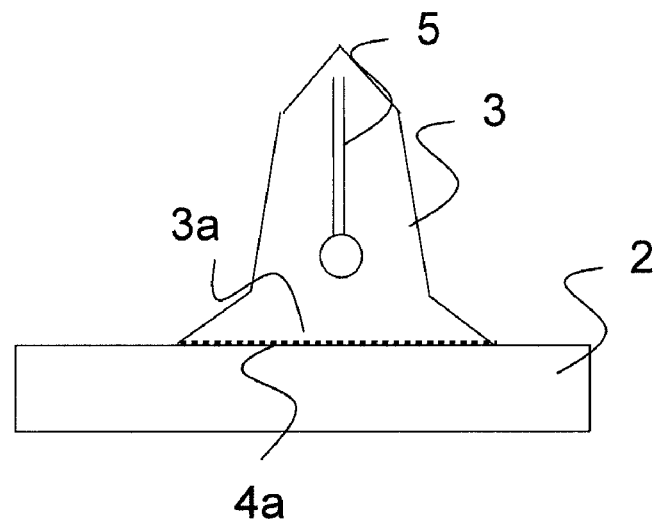
FIG. 4 is a schematic diagram of a microsampler with a bending site on a lancet body.

FIG. 4 shows a lancet tip 3 with an integrated microsampler 5. The lancet tip 3 with an integrated microsampler 5 can be bent by means of a bending line 4a at the proximal end 3a of the lancet tip 3.

Figure 5:
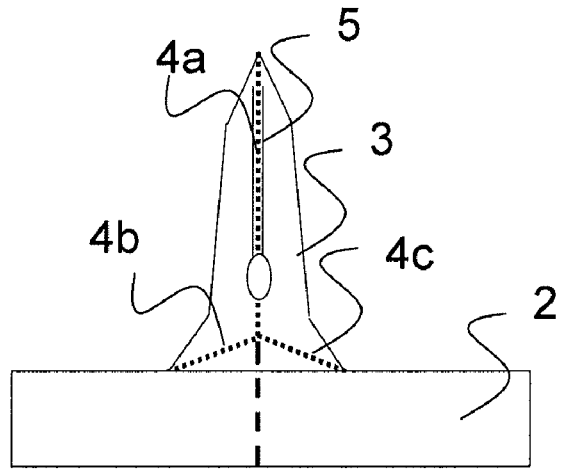
FIG. 5 is a schematic diagram of a microsampler with an impressed bending region on a lancet body.

FIG. 5 shows a special embodiment of the lancet tip 3 with an integrated microsampler 5 where there are several bending lines 4a, 4b and 4c as in FIG. 3.

Figure 6:
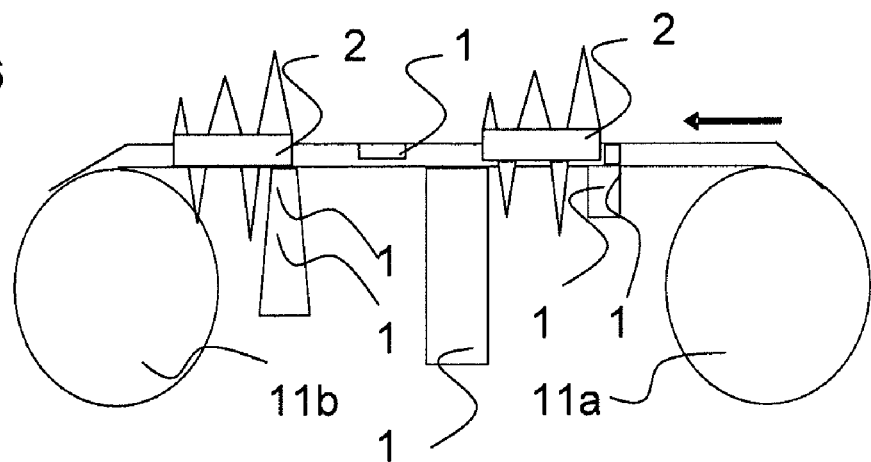
FIG. 6 is a schematic diagram of a system containing a carrier tape on which lancets are attached, comprising selection means, lancing means and an optical system.

FIG. 6 shows a system with a carrier tape 10 which is wound onto two different rolls 11a and 11b where one of the rolls 11a can contain unused lancets 1 or test elements 13 whereas roll 11b stores used lancets 1 or test elements. The system can additionally have a bending element 12 which, after selecting the appropriate lancing tip 3, bends the lancet. In this case the bending element 12 serves as the selection means 16. In addition the system can contain an optical system 14 as well as means for driving the lancet such as a pusher 15. The optical system 14 can also be used as a selection means 16 when it is configured as a sensor for a mark on the carrier tape 10 or on the lancet body 2 with lancet tips 3.

Figure 7A:
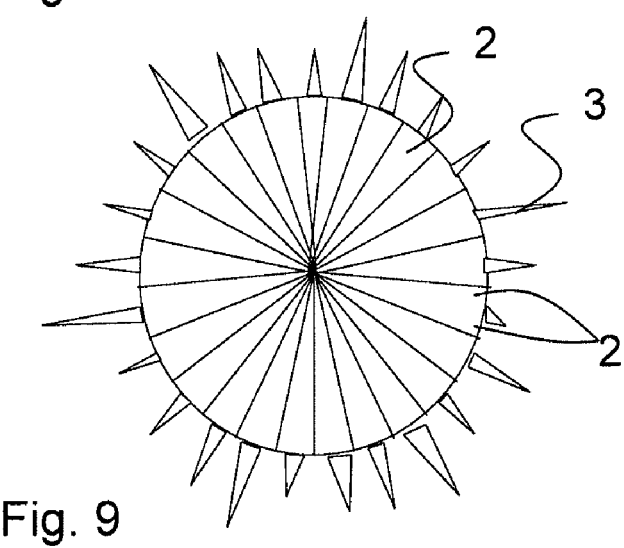
FIG. 7a is a schematic diagram of a circular arrangement of different lancets which have different lengths or different bending regions.
Figure 9:
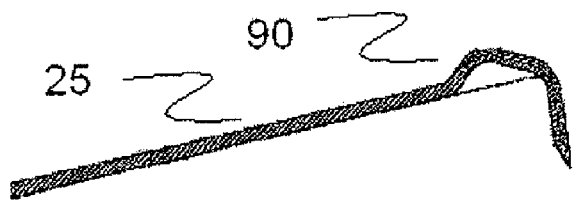
FIG. 9 is a schematic diagram of a lancet wheel which is moved by eccentric rollers.
Figure 8A:
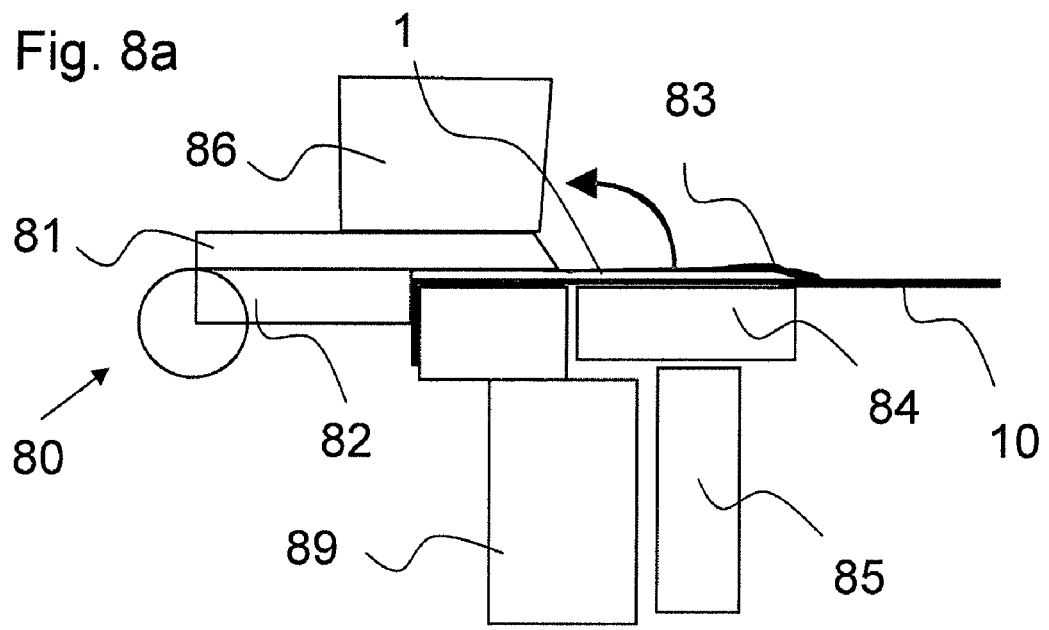
FIGS. 8 a-d are schematic diagrams of a bending process before the lancing process with the aid of a bending device which also contains a bending-back element.
Figure 8B:
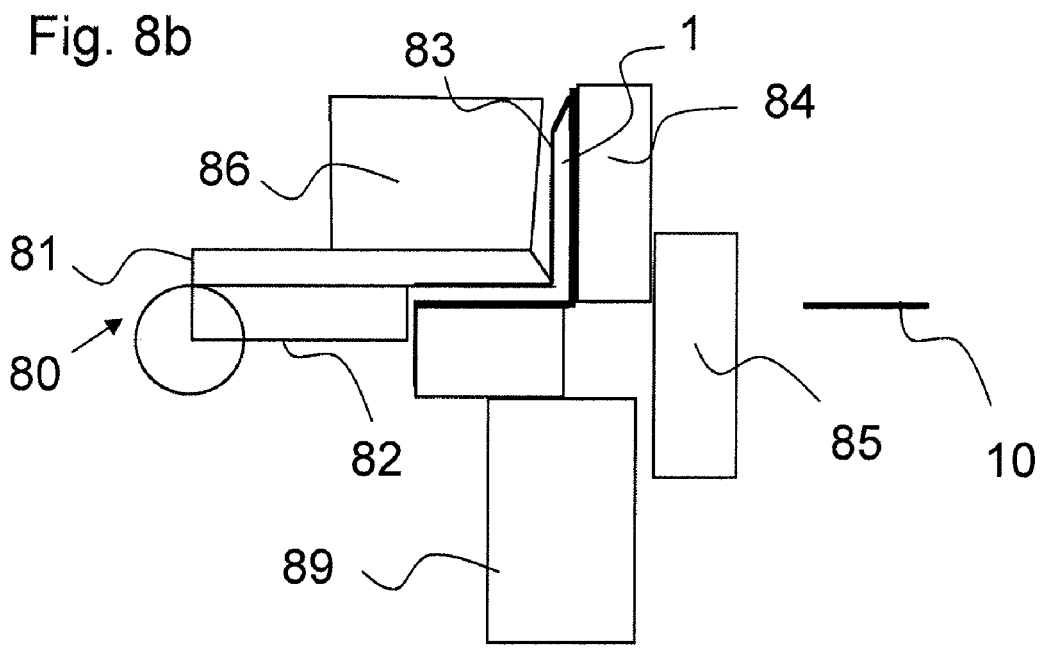
Figure 8C:
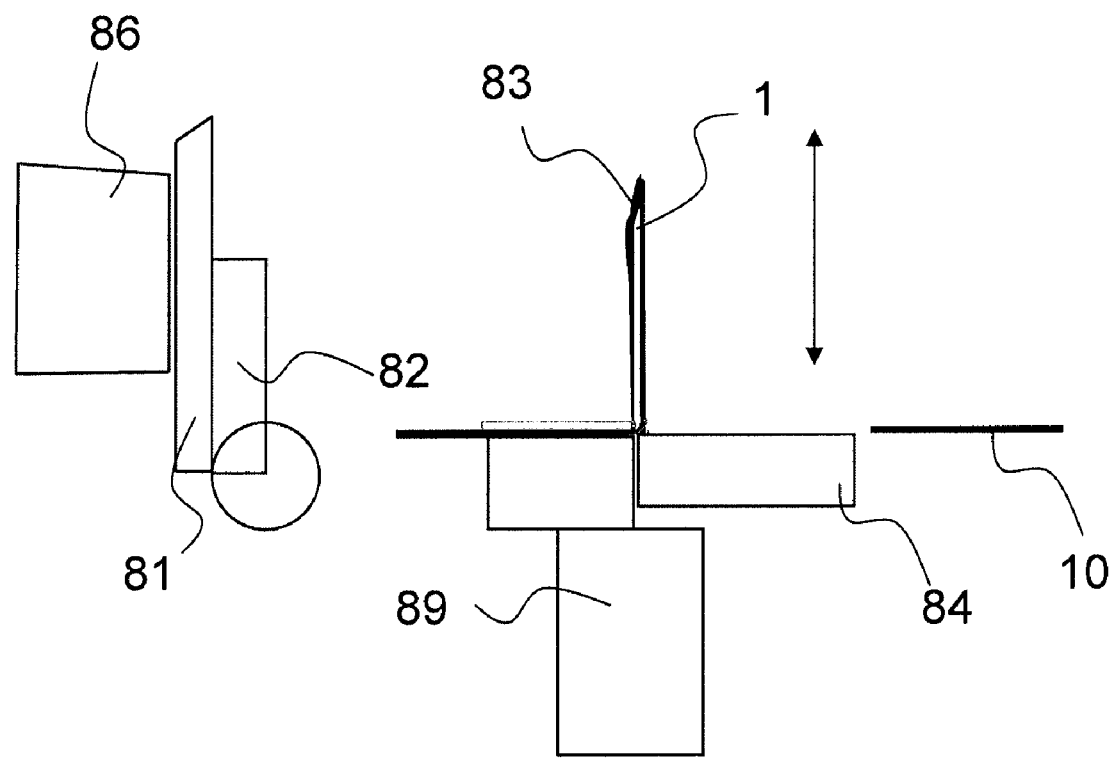
Figure 8D:
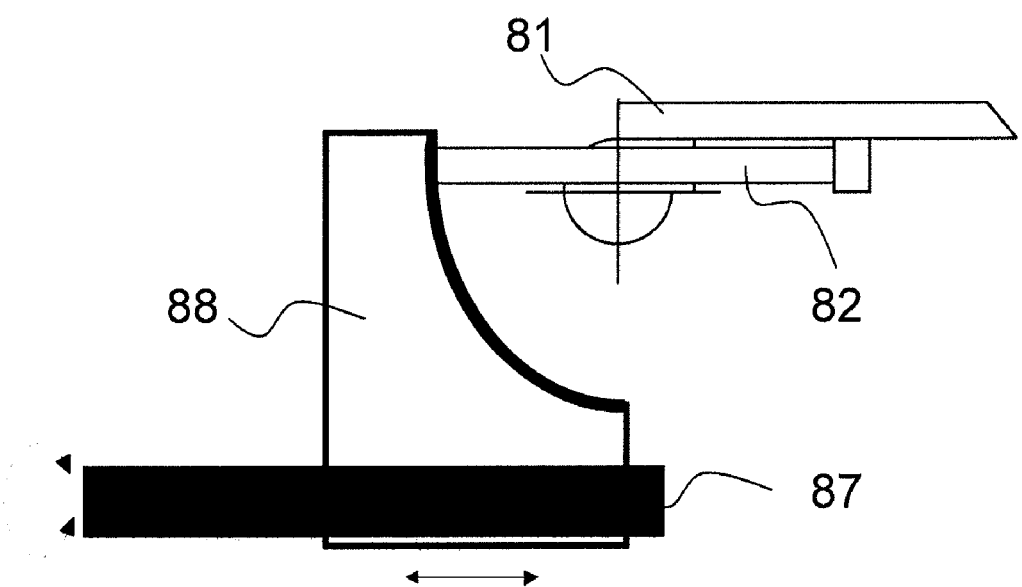

FIG. 7a shows a circular arrangement of lancet tips 3 and lancet carriers 23 in the form of a lancet wheel 24. In this case the lancet tips 3 can be bent towards the lancet carrier 23 and also have different lengths. The lancet carriers 23 can be separated from one another by grooves so that each lancet arm 25 can be deflected out of the plane of the circular lancet 1. This can be used to execute the lancing process. In this process the lancet arm 25 in turn executes a circular movement during the lancing. The lancet arm 25 can have bars 26 which limit the lancing depth because during lancing they prevent further penetration of the lancet into the body. Due to an appropriate pre-bending of the lancet arms 25, the lancet returns automatically into its original position after the lancing as shown in FIG. 9. Due to its flexibility, the lancet arm 25 can be deflected upwards as well as downwards. Since the lancet arm 25 executes a circular movement during the lancing movement, the body of the user is not punctured perpendicularly but rather in a circular movement. As a consequence force is not only exerted vertically on the skin but rather lateral forces also act. As a result, the pain during lancing is greater than with a conventional lancet which is inserted perpendicularly into the skin. In order to reduce these lateral forces during the lancing process, the lancet tip 3 of the lancet 1 can have a blade 70 which slits the skin of the body and does not puncture the skin as is the case with conventional lancets.

Figure 7B:
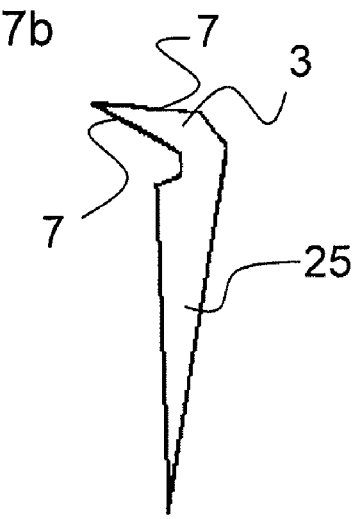
FIG. 7b is a schematic diagram of a lancet arm with a blade at the distal end of the lancet.

FIG. 7b shows a lancet 1 which has a blade 70 at its distal end 3b. In contrast to a lancet tip 3 (as shown in the previous figures), the blade 70 does not have edges which converge uniformly and merge into the tip 3. In the case of the blade 70 the edges 71 and 72 of the blade 70 converge towards the tip 73 at different angles. Depending on the arrangement of the blade 70 to the lancet body 25, the first side edge 71 and the second side edge 72 can run in the plane of the orbit or at right angles thereto. If the side edges 71 and 72 are arranged in the plane of the orbit, the ground side edges 71 and 72 can cut in the direction of movement whereas the side edges 71 and 72 disposed at right angles to the orbit can also cut transversely to the direction of movement which can lead to more pain during lancing. A wheel configured similarly to the lancet wheel 24 can also be designed for test elements which can be arranged together with the lancet wheel 24 in a system in such a manner that the lancing and blood transfer can be carried out at one opening.

A device is shown schematically in FIGS. 8 a-d which shows the bending before the puncture and the bending back after the puncture. This device is preferably used with lancets which are attached to a carrier tape 10. It can, however, also be used for lancets which are not attached to a carrier tape 10. For the lancing process, the lancet 1 should be bent out of the carrier tape plane. This state is shown in FIG. 8a. For this purpose the carrier tape 10 is clamped between the bottom part 82 and the upper part 81 of the holding element 80 and the pusher 89. As a result, a part of the carrier tape 10 is bent over which prevents it from slipping during the bending process. Subsequently, the lancet 1 is bent at a predefined position with the aid of a tilting element 84 which is driven by a pusher 85. In this process, the tilting element 84 exerts so much pressure on the lancet that it bends at the site at which it touches the upper part 81 of the holding element 80 as shown in FIG. 8b. As shown in FIG. 8c, the holding element 80 releases its hold on the carrier tape 10 after the bending process and the holding element 80 can be rotated out of the plane of the carrier tape in order not to hinder the lancing process. The lancet 1 can be moved for the lancing by moving the pusher. In order to be able to influence the lancing depth during the lancing process, the holding element 80 is connected to a carriage 88 which can displace the holding element 80 which in this case serves as a reference element for adjusting the lancing depth. As a result of the displacement of the holding element 80, the upper part 81 of the holding element 80 is shifted to a greater or lesser extent over the carrier tape 10 towards the lancet tip. As a result of this shift, the lancet tip has a different length after the bending process depending on the extent to which the holding element 80 has been shifted forwards or backwards. The shifting of the carriage 88 can preferably be executed by a displacement thread 87. In addition, a bending-back element 86 can be attached to the holding element 80 which bends the lancet 1 back again into the carrier tape plane after the lancet 1 has been inserted into the body.

FIG. 9 shows a lancet arm 25 which has a curvature 93 which projects slightly out of the plane of the lancet arm 25. The channel of the microsampler can be located in this curvature. This allows a test element to be moved in a simple manner to the curvature in order to transfer the blood which has collected in the channel of the microsampler.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMERALS 1 lancet
2 lancet body
3 lancet tip
3a proximal end
3b distal end
4a first bending line
4b second bending line
4c third bending line
5 microsampler
10 carrier tape
11a first roll
11b second roll
12 bending element
13 test elements
14 optical system
15 pusher
16 selection means
23 lancet carrier
24 lancet wheel
25 lancet arm
26 bar
70 blade
71 first cutting edge
72 second cutting edge
80 holding element
81 upper part of holding element
82 lower part of holding element
83 sterile protection
84 tilting element
85 pusher
86 bending-back element
87 displacement thread
88 carriage
89 pusher
90 curvature

What is claimed is:

1. A device for collecting body fluid, comprising:
at least one lancet comprising a lancet body, the lancet body having at least two tips for lancing the skin of a patient, the at least two tips comprising a first tip having a first length and a second tip having a second length that is different from the first length;
a selection means for selecting one of the at least two tips for a lancing process and thereby selecting a defined lancing depth, wherein the unselected tip is positioned in the device and unused during the lancing process; and
a lancet drive for driving the selected lancet tip in a puncture movement.

2. The device of claim 1, wherein the at least two tips are oriented in different directions on the lancet body.

3. The device of claim 1, wherein the at least two tips are arranged in the shape of a star on the lancet body.

4. The device of claim 1, wherein the at least two tips are arranged linearly on the lancet body.

5. The device of claim 1, further comprising a bending device which changes the alignment of the tips relative to the lancet body.

6. The device of claim 1, wherein the alignment of at least one tip can be changed relative to the lancet body.

7. The device of claim 1, wherein the at least one lancet is a flat lancet.

8. The device of claim 1, wherein the at least two tips comprise a bending region.

9. The device of claim 8, wherein the bending region extends over a region of the tip.

10. The device of claim 8, wherein when a threshold force acts on the lancet, areas adjoining or within the bending region bend.

11. The device of claim 1, further comprising a carrier tape on which the at least one lancet is arranged.

12. The device of claim 11, wherein the at least one lancet comprises different orientations on the carrier tape.

13. The device of claim 11, further comprising at least one test element arranged on the carrier tape.

14. The device of claim 11, wherein a proximal end of the at least one lancet is attached to the carrier tape.

15. The device of claim 1, wherein the lancet tips comprise a sterile protection.

16. The device of claim 1, further comprising a means for returning bent tips to an original position.

17. The device of claim 1, further comprising a test element.

18. The device of claim 1, further comprising a detection unit.

19. A lancing device for insertion of a lancet tip into a body part, comprising a lancet body with at least two tips for lancing the skin of a patient, the at least two tips comprising a first tip having a first length and a second tip having a second length that is different from the first length, wherein when one tip of the at least two tips is selected, a lancing process takes place with a defined lancing depth depending on the length of the selected tip, further wherein at least one of the unselected tips is positioned relative to the selected tip in the device during the lancing process such that no lancing process is executed with the unselected tip, the device further comprising a drive unit for driving the selected lancet tip in a puncture movement.

20. The lancing device of claim 19, wherein a tip can be selected by means of a bending region in the lancet body.

21. The lancing device of claim 19, wherein the lancet body has a coupling element configured to couple the lancet body to a drive unit of a blood collection system.

22. The lancing device of claim 21, wherein the coupling element allows the lancet body to be coupled in different positions relative to the drive unit.

23. The lancing device of claim 21, wherein the coupling element comprises a plurality of coupling elements.

24. The lancing device of claim 21, wherein the lancet tips comprise different orientations.

25. A method of using a lancing device comprising a lancet body and at least two tips for lancing the skin of a patient, the at least two tips comprising a first tip having a first length and a second tip having a second length that is different from the first length, the method comprising:
- selecting a desired lancing depth;
- selecting one of the at least two tips that corresponds to the desired lancing depth; and
- with the aid of a lancet drive, performing a lancing process with the selected one of the tips while maintaining the unselected tip or tips positioned in the device and unused during the lancing process.

26. The method of claim 25, further comprising bending the selected lancet.

27. The method of claim 26, wherein the bending occurs along a bending region.

28. The method of claim 25, further comprising changing the alignment of the selected tip relative to the lancet body.

29. The method of claim 25, wherein the at least two tips point in different directions during the lancing process.

30. The method of claim 25, further comprising bending the selected tip out of a lancet body plane.

31. The method of claim 25, further comprising, after the performing of the lancing process with the selected one of the tips, bending the selected tip back into a carrier plane.

* * * * *